United States Patent [19]
Knoepfler

[11] Patent Number: 5,217,460
[45] Date of Patent: Jun. 8, 1993

[54] MULTIPLE PURPOSE FORCEPS

[76] Inventor: Dennis J. Knoepfler, 1383 Whitaker La., Amelia, Ohio 45102

[21] Appl. No.: 673,659

[22] Filed: Mar. 22, 1991

[51] Int. Cl.$^5$ .................... A61B 17/00; A61B 19/00
[52] U.S. Cl. ............................. 606/52; 606/1; 606/2; 606/46; 606/205; 606/207; 606/208
[58] Field of Search ................ 604/20, 21, 22; 606/1, 606/2, 13, 14, 15, 27, 46, 51, 52, 127, 205, 206, 207, 208, 209, 128

[56] References Cited

U.S. PATENT DOCUMENTS

| | | |
|---|---|---|
| 724,046 | 3/1903 | Sampson . |
| 2,541,246 | 2/1951 | Held . |
| 3,709,215 | 1/1973 | Richmond . |
| 3,783,873 | 1/1974 | Jacobs ................................. 606/208 |
| 3,916,909 | 11/1975 | Kletschka et al. ................... 606/211 |
| 4,128,099 | 12/1978 | Bauer ................................... 606/52 |
| 4,249,533 | 2/1981 | Komiya ............................... 606/15 |
| 4,608,982 | 9/1986 | Pollard ................................ 606/207 |
| 4,643,190 | 2/1987 | Heimberger . |
| 4,646,751 | 3/1987 | Maslanka . |
| 4,662,371 | 5/1987 | Whipple et al. .................... 604/22 |
| 4,759,348 | 7/1988 | Cawood .............................. 606/207 |
| 4,763,669 | 8/1988 | Jaeger . |

FOREIGN PATENT DOCUMENTS

| | | | |
|---|---|---|---|
| 0316816 | 5/1989 | European Pat. Off. | ............ 606/205 |
| 2550693 | 5/1977 | Fed. Rep. of Germany | ........ 606/13 |
| 2821264 | 11/1978 | Fed. Rep. of Germany | ........ 606/15 |
| 0143033 | 7/1980 | Fed. Rep. of Germany | ........ 606/205 |
| 2017506 | 10/1979 | United Kingdom | .................. 606/15 |
| 9010420 | 9/1990 | World Int. Prop. O. | .......... 606/205 |

OTHER PUBLICATIONS

Solos Endoscopy Catalog 1990.
Jarit Laproscopic Catalog 1991.
Jarit Instrument Update Dec. 1990.
Birtcher Safety Tips Probes Flyer.

Primary Examiner—Stephen C. Pellegrino
Assistant Examiner—Glenn Dawson
Attorney, Agent, or Firm—Wood, Herron & Evans

[57] ABSTRACT

A multiple purpose medical forceps allows for simultaneous grasping of tissue while lasing, irrigating, suctioning and cauterizing. The forceps includes a laser fiber and irrigation and suction catheters contained within a tubular housing and exiting adjacent a pair of jaws. The forceps is insertable through a cannula into a patient's abdomen for use during a laparascopy, or into any other bodily cavity where scopic surgery may be performed.

15 Claims, 2 Drawing Sheets

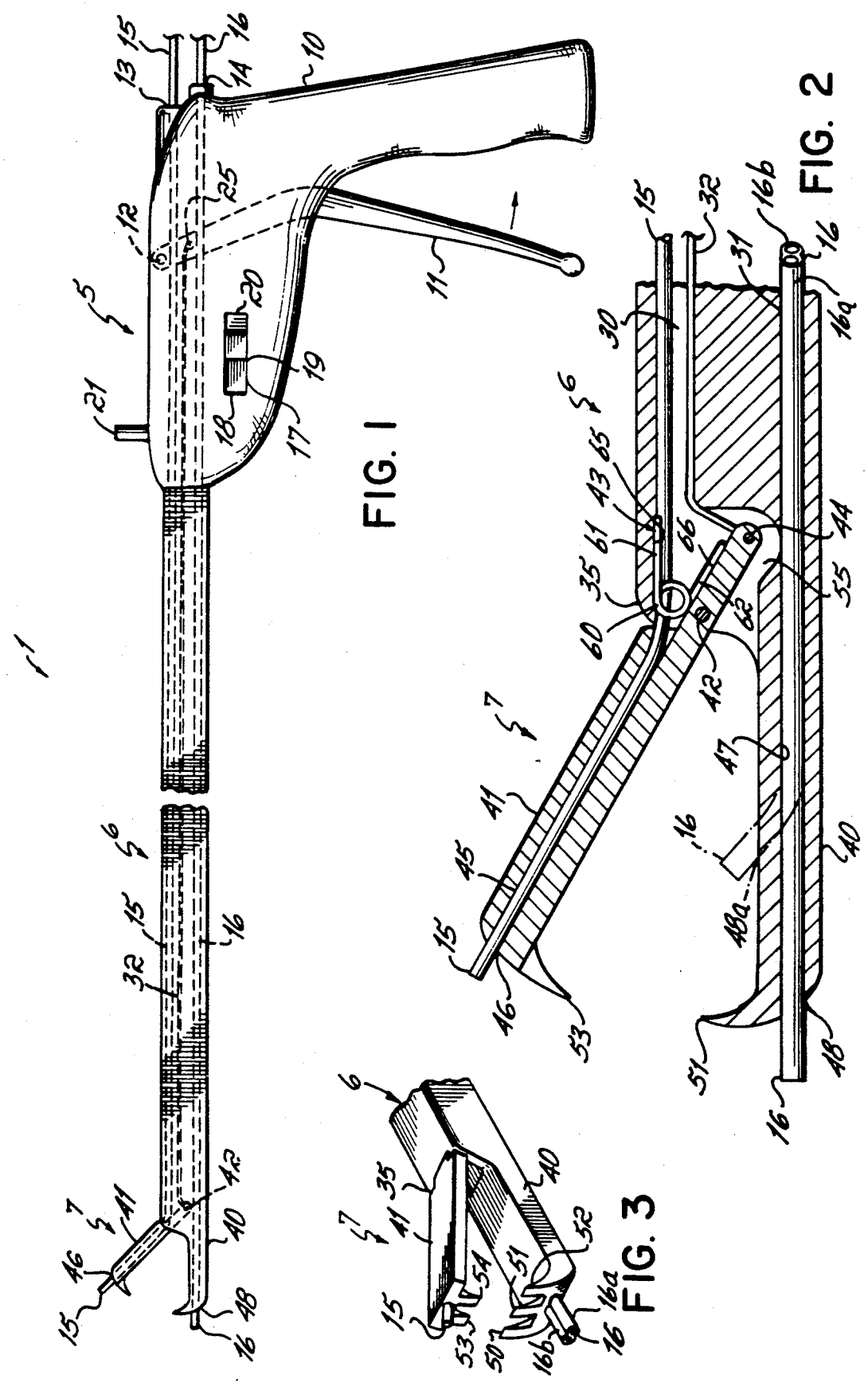

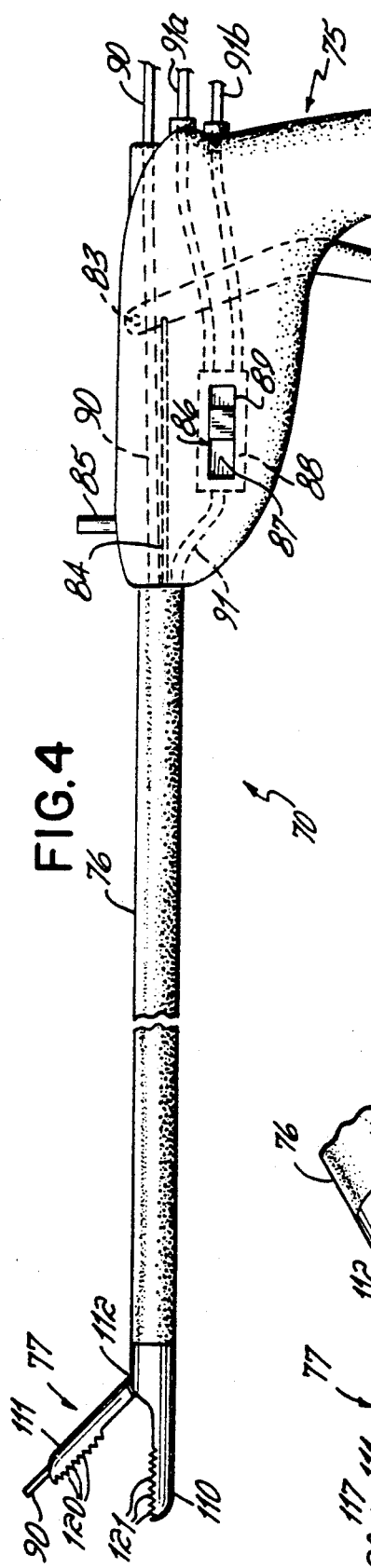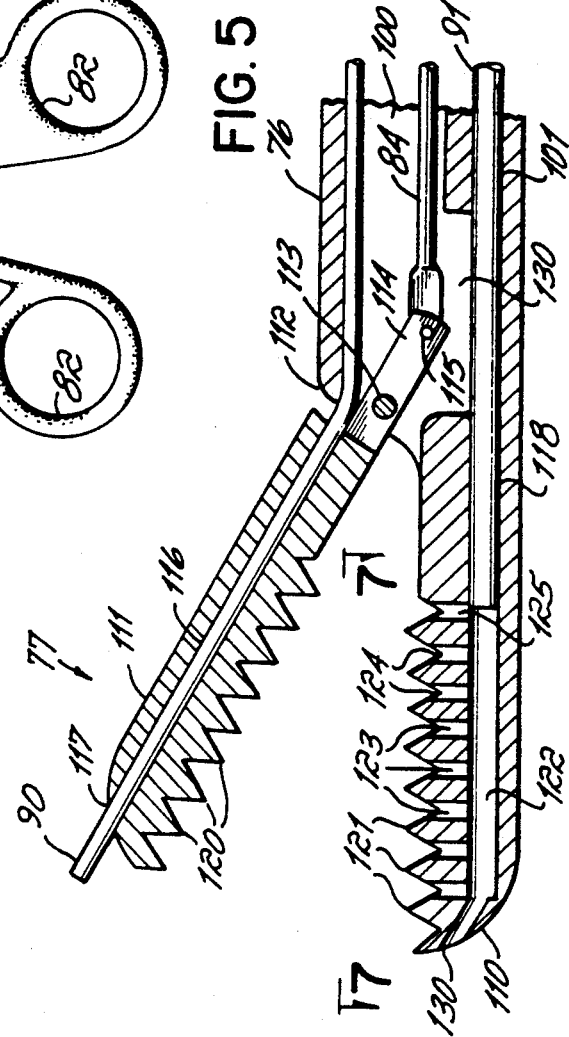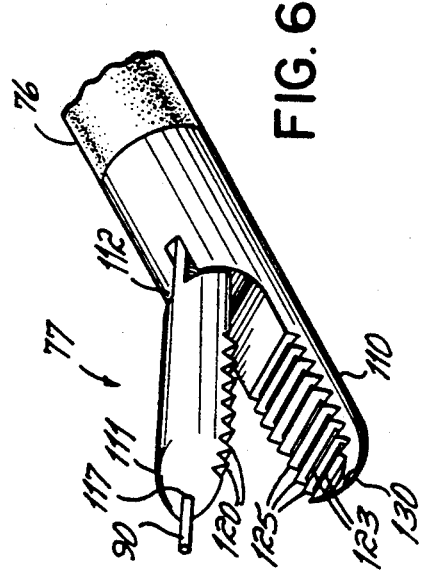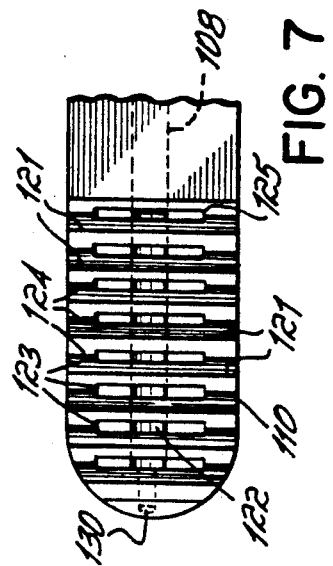

5,217,460

MULTIPLE PURPOSE FORCEPS

BACKGROUND OF THE INVENTION

1. Field of the Invention

This invention relates generally to medical instruments, and more particularly to a medical instrument for use during any scopic surgery.

2. Description of the Prior Art

In a scopic procedure, a medical instrument is inserted through a slender, cylindrical cannula, or sleeve, and into the patient's bodily cavity. Many different scopic surgeries, such as laparoscopy, thorascopy, cranioscopy, pelvoscopy, and arthroscopy, require the use of such instruments. Should multiple instruments be needed for a particular scopic procedure, it is necessary to have multiple portal entries into the patient's bodily cavity with each fitted with a cannula for insertion of a medical instrument therethrough. During a scopic procedure, it is not uncommon to perform many separate tasks, such as grasping of tissue, dissecting, lasing, irrigating, suctioning, and cauterizing or coagulating. It will be appreciated that each of these separate procedures has in the past required a specialized instrument.

It is desirable to have a multiple purpose instrument capable of performing a plurality of procedures during any scopic surgery. Specifically, it is desirable to combine lasing, irrigating, suctioning and cauterizing features with a medical forceps to allow for simultaneous grasping of tissue or dissecting while selectively lasing, irrigating, suctioning and cauterizing. This would require only one portal entry into the patient's bodily cavity, yet would permit a surgeon to perform numerous procedures quickly and efficiently.

SUMMARY OF THE INVENTION

It is therefore an object of the present invention to provide a universal surgical instrument that can be used during any scopic surgery that can serve many functions.

It is another object of the present invention to provide a multiple purpose medical instrument wherein the need for many surgical portal entries for various devices is eliminated.

It is a further object of the present invention to provide a multiple purpose forceps which obviates the need for a plurality of medical instruments for performing scopic procedures.

The present invention is a multiple purpose medical forceps for use during scopic surgery which requires only a single portal entry into the patient's bodily cavity.

A preferred embodiment of the multiple purpose forceps of the present invention comprises a tubular housing with a handle attached to one end, a jaw pair attached to the other end, and jaw actuation means for opening and closing the jaw pair via the handle. The multiple purpose forceps further includes the capability for lasing, irrigating, suctioning and cauterizing during a scopic surgery. Preferably, a laser fiber and irrigation and suction catheters extend from the handle through the housing and to the jaw pair, such that these are contained completely within the forcep's housing.

It is preferable that the laser fiber extend through the housing and one of the jaw elements, and exit at a forward tip of the jaw. The irrigation and suction catheter extends through the housing and the second jaw element, and exits at a forward tip of the jaw. Alternatively, the irrigation and suction catheter could exit the second jaw element medially along its length. Or, if used in conjunction with a jaw having "open" type serrated teeth, the irrigation and suction catheter could simply terminate at the base of the jaw, thereby providing continuous irrigation and suction between these teeth and along the length of the jaw.

The present invention further includes a switch for actuating the irrigation and suction catheters and which is mounted on the handle. A bipolar port is included on the handle as well to connect a standard cauterization device to the forceps. In this manner, a user of the instrument may simultaneously open and close the jaws while lasing, irrigating, suctioning and cauterizing as needed.

One advantage of the present invention is that the need for multiple portal entries during a scopic surgical procedure has been eliminated.

Another advantage of the present invention is that the need for multiple medical instruments to perform a scopic surgical procedure has been eliminated.

Yet another advantage of the present invention is that grasping of tissue, dissecting, suctioning, irrigating, lasing and coagulating may be performed with one instrument, and with one hand.

Still another advantage of the present invention is that the breaking up of large blood clots into smaller pieces small enough to be suctioned through the serrated teeth is facilitated.

These and other objects and advantages of the present invention will become more apparent to those having ordinary skill in the art to which the invention relates from the following description taken in conjunction with the accompanying drawings herein, in which:

BRIEF DESCRIPTION OF THE DRAWINGS

FIG. 1 is a side view of the multiple purpose forceps of the present invention;

FIG. 2 is an enlarged view of the jaw pair of the present invention illustrating the jaw pair with laser, irrigation and suction channels;

FIG. 3 is a perspective view of the jaw pair of the present invention;

FIG. 4 is a side view of an alternative embodiment of the multiple purpose forceps of the present invention;

FIG. 5 is an enlarged view of the jaw pair of the alternative embodiment of the present invention illustrating the jaw pair with laser, irrigation and suction channels;

FIG. 6 is a perspective view of the jaw pair of the alternative embodiment of the present invention; and FIG. 7 is a view taken along lines 7—7 of FIG. 5.

DESCRIPTION OF THE PREFERRED EMBODIMENTS

Referring first to FIG. 1, one embodiment of a multiple purpose medical forceps 1 is illustrated. The forceps 1 may be fabricated from stainless steel and comprises generally a handle 5, a tubular housing 6, and a jaw pair 7. Alternatively, the forceps 1 could be fabricated from less expensive rigid plastic should disposability be desired.

The handle 5 is in the form of a pistol grip style handle having a handle portion or grip 10 and a trigger style actuation lever 11. The lever 11 is hingedly connected to the handle grip 10 via pin 12 within the grip 10. A jaw actuation rod or cable 32 is connected to the lever 11 at 25. The handle grip 10 further includes apertures 13 and 14 for insertion therein of a laser fiber 15 and an irrigation and suction catheter 16. The catheter 16 includes an irrigation side 16a and a suction side 16b.

A three position rocker switch 17 is employed to activate the irrigation and suction catheter 16. A first position 18 activates the irrigation mode, a middle or neutral position 19 deactivates both irrigation and suction modes, and a second position 20 activates the suction mode. The rocker switch 17 is operable to engage a conventional dual gate valve (not shown) which, in its middle or neutral position, blocks the irrigation orifice 16a and the suction orifice 16b. When the rocker switch 17 is placed in the first position 18 a first gate valve is withdrawn from over the irrigation orifice 16a to allow passage of irrigating fluid therethrough. Returning the rocker switch 17 to the middle or neutral position 19 causes this first gate valve to return to its closed position over the irrigation orifice 16a. Placing the rocker switch 17 in the second position 20 withdraws a second gate valve from over the suction orifice 16b, allowing the pressure differential of the vacuum to suction the work area. Placing the rocker switch 17 back to its middle or neutral position 19 causes this second gate valve to close back over the suction orifice 16b and thereby terminating this suctioning action.

The handle 5 further includes a bipolar plug 21 for connection to a standard cauterization device (not shown). The forward tip of the jaw pair 7 may be utilized to conduct electricity generated by the cauterization device to the work area for searing, cauterizing and the like. In such a case, the entire instrument 1 should be coated with an insulating substance, such as a thin film of rubber or vinyl. Should the instrument 1 be a plastic disposable type, a simple conducting wire could be included within the housing 6 spanning between the bipolar plug 21 and the forward tip of the jaw pair 7 to conduct electricity from the cauterization device for cauterizing a work area.

The housing 6 is essentially a slender tube that is operable for placement through an 8-10 mm port. With reference to FIGS. 1 and 2, it will be seen that the housing 6 includes an upper channel 30 and a lower channel 31. The upper channel 30 provides a path through which the laser fiber 15 may travel the entire length of the housing 6 while being contained therein. The upper channel 30 further provides a path through which the jaw actuation cable 32 may span between the jaw pair 7 and the trigger lever 11. The lower channel 31 provides a path through which the irrigation and suction catheter 16 may travel the entire length of the housing 6 while likewise being entirely contained therein.

With reference to FIGS. 2 and 3, it will be seen that the jaw pair 7 is comprised of a first fixed jaw element 40 which is essentially an extension of a lower portion of the housing 6, and a second movable or pivotable jaw element 41. The forward tip of the jaw pair 7 is spherically shaped to allow for ease of insertion through a cannula.

Jaw 41 is connected to a forward end 35 of the housing 6 by a pin 42. Jaw 41 is thereby operable to pivot or move relative to jaw 40. Jaw 41 is further spring loaded into an open position by way of a helical torsion spring 43. Torsion spring 43 includes a helical spring portion 60 and actuation arms 61 and 62. Arm 61 is positioned adjacent an upper surface 65 of the channel 30 near a forward end thereof. Arm 62 is positioned adjacent an upper surface 66 of the jaw 41 near an aft end thereof. The jaw cable 32 is attached to the jaw 41 at end 44. A relieved area 55 is provided to allow for complete rotational travel of the jaw 41.

Jaw 41 further includes a channel 45 providing a path through which the laser fiber 15 may be inserted. This channel 45 has an exit port 46 at a forward tip of the jaw 41 from which the laser fiber 15 may exit. The fixed jaw 40 includes a similar channel 47 which is essentially an extension of the channel 31 contained within the housing 6. This channel 47 provides a path through which the irrigation and suction catheter 16 may pass through the fixed jaw 40. Channel 47 has an exit port 48 at a forward tip of the jaw 40 from which the irrigation and suction catheter 16 may exit. Alternatively, the catheter 16 (shown in phantom) may exit the jaw 40 at exit port 48a located medially along the length of the jaw 40.

The fixed jaw 40 further includes three teeth 50, 51 and 52 which are cooperable with two teeth 53 and 54 in the rotating jaw 41 for grasping tissue and the like.

It will be appreciated that while one embodiment of a jaw element has been illustrated, many different jaw elements may be substituted depending on the particular application or scopic procedure. Furthermore, no switch means has been shown on the handle 5 for actuating the laser, since most lasers are operated from a remote location by, for example, a foot pedal. However, most nearly any switch means could nonetheless be incorporated on the handle 5 for activating the laser should it be desirable to do so.

Describing now the operation of the present invention, the trigger lever 11 is pulled rearwardly thereby translating the jaw actuation cable 32 rearwardly, compressing the spring 43 and effectively moving jaw 41 downwardly into a closed position. It will be appreciated that when the jaw 41 is rotated to its fully closed position, the profile of the jaw element 7 is no larger than that of the housing 6. In this configuration, the instrument 1 may readily be inserted through a cannula into, for example, a patient's abdomen, for performing a laparoscopy.

After insertion through the cannula, the multiple purpose forceps 1 may be used for many different functions, such as bluntly dissecting out a duct or blood vessel (artery or vein), grasping tissue and the like, all the while irrigating and suctioning as often as necessary. Furthermore, one may lase or coagulate where necessary to dissect or gain hemostasis.

It will be appreciated that changing the angle of the rotating jaw 41 effectively will change the angle of the application of a laser beam exiting the laser fiber 15. And, it will be appreciated that the irrigation and suction catheter 16 will be maintained in a path which is substantially colinear with and forward of the housing 6 of the instrument 1. Or, should alternative exit port 48a be utilized, the irrigation and suction catheter 16 will be maintained in a position substantially between the fixed jaw 40 and the movable jaw 41.

An alternative, and perhaps preferred embodiment of the present invention is illustrated in FIG. 4. The forceps 70 includes a pistol grip style handle 75, a cylindrical tubular shaft or housing 76, and a jaw pair 77.

The pistol grip handle 75 includes a handle portion or grip 81 and a trigger actuation lever 80, each of which is outfitted with a thumb or finger receiving loop 82. The lever 80 of the handle 75 is pivotally connected to the handle grip 81 by way of pivot 83. Handle grip 81 is itself made an integral part of the shaft 76 by any conventional means. The lever 80 has attached to an upper end thereof a rearwardmost end of a jaw pair actuation rod 84. A bipolar plug 85 is included as part of the handle grip 81 for connection to a standard cauterization device, similar to that of the primary embodiment of FIG. 1. A three position rocker switch 86, likewise similar to that of the primary embodiment of FIG. 1, is fixedly attached to the grip 81 and includes a first position 87 which activates the irrigation mode, a middle or neutral position 88 which deactivates both irrigation and suction modes, and a second position 89 which activates the suction mode. A laser fiber 90 is threadably inserted through a hole (not shown) in the upper end of the handle grip 81 and through the housing 76. Suction catheter 91b and irrigation catheter 91a supply the irrigation/suction catheter 91 via operation of the rocker switch 86.

The housing 76 is essentially a slender tube similar to that of the primary embodiment of FIG. 1, however it is illustrated as being cylindrical which may facilitate placement through an 8-10 millimeter cannula or port. With reference to FIGS. 4 and 5, it will be seen that the housing 76 includes an upper channel 100 and a lower channel 101. The upper channel 100 provides a path through which the laser fiber 90 may travel the entire length of the housing 76 while being contained therein. The upper channel 100 further provides a path through which the jaw actuation rod 84 may span between the jaw pair 77 and the handle grip 81. The lower channel 101 provides a path through which irrigation and suction catheter 91 may travel entirely through the housing 76 while likewise being entirely contained therein.

With reference to FIGS. 4 and 5, it will be seen that the jaw pair 77 is comprised of a first fixed jaw element 110, which is essentially an extension of lower portion of the housing 76, and a second movable or pivotable jaw element 111.

Jaw 111 is connected to a forward end 112 of the housing 76 by pin 113. Jaw 111 is thereby operable to pivot or move relative to jaw 110. The jaw actuation rod 84 is attached to the jaw 111 at end 114 by way of pivot 115 A relieved area 130 is provided for complete rotational travel of the jaw 111. Since the jaw pair 77 may easily be opened and closed with one hand by utilizing the loops 82 on the handle halves 80 and 81, no spring means is utilized in this embodiment to spring load the jaw pair 77 into an open position.

Jaw 111 further includes a channel 116 providing a path through which the laser fiber 90 may be inserted. This channel 116 has an exit port 117 at a forward tip of the jaw 111 from which the laser fiber 90 may exit. The fixed jaw 110 includes a similar channel 118 which is essentially an extension of the channel 101 contained within the housing 76. This channel 118 provides a path through which the irrigation and suction catheter 91 may pass through the fixed jaw 110.

The movable jaw 111 contains a plurality of serrated teeth 120 which extend transversely across the width of the jaw 111. These teeth 120 of the movable jaw 111 complementarily fit together with a plurality of teeth 121 of the fixed jaw 110, these teeth 120 likewise being serrated and extending transversely across the width of the jaw 110. Beneath the teeth 121 of the fixed jaw 110 is a cavity 122 which essentially is an extension of the channel 118 contained within the fixed jaw 110. A plurality of voids 123 are machined into the valleys 124 between the serrated teeth 121 to allow for irrigation and suction communication through and along the entire length of the jaw 110 between the teeth 121. The irrigation and suction catheter 91 is positioned to terminate slightly rearward of the first void 125, and is thereby in a position to irrigate and suction through each of the voids 123 along the length of the jaw 110. This feature may perhaps be best visualized with reference to FIGS. 5 and 7. The cavity 122 exits the jaw 110 at 130. In this manner, when the jaw pair 77 is closed, one may irrigate and suction directly through this port 130, rather than through the teeth 121. It will be appreciated that the serrated teeth function to break up blood clots and the like so as to be suctionable through these teeth.

The operation of the alternative embodiment of the present invention is much the same as the primary embodiment as hereinabove described. The primary difference is that one may irrigate and suction between the teeth 121 of the lower fixed jaw 110 while simultaneously grasping, etc.

While I have described only two embodiments of my invention, those skilled in the art will readily recognize adaptations and modifications which can be made and which will result in an improved medical instrument, yet without departing from the spirit or scope of the invention as defined in the appended claims. Therefore, I intend for my invention to be limited only by the claims.

What is claimed is:

1. A multiple purpose forceps comprising:
   a handle,
   a tubular housing,
   a jaw pair,
   jaw actuation means,
   laser means,
   irrigation means,
   suction means, and
   cauterization means;
   said housing having a first end to which is attached said handle and a second end to which is attached said jaw pair, said jaw pair having first and second jaw elements, said jaw actuation means extending from said handle through said housing to said jaw pair and operable to actuate said jaw pair, said laser, irrigation, suction and cauterization means extending from said handle through said housing and at least partially through one of said jaw elements of said jaw pair, said forceps being operable to grasp, lase, irrigate, suction and cauterize through a single portal entry.

2. The multiple purpose forceps of claim 1 wherein said laser means extends through said first jaw element to a forward tip thereof.

3. The multiple purpose forceps of claim 1 wherein said irrigation and suction means extends through said second jaw element to a forward tip thereof.

4. The multiple purpose forceps of claim 1 wherein said irrigation and suction means extends partially through said second jaw element and exits generally medially along a length thereof.

5. The multiple purpose forceps of claim 1 wherein said irrigation and suction means are actuated by switch means on said handle.

6. A surgical device comprising a jaw pair in combination with means for actuating said jaw pair, said jaw pair comprising a first fixed jaw element and a second movable jaw element, said second movable jaw element being pivotally connected to said first fixed jaw element, one of said jaw elements having a laser fiber passing therethrough and exiting at a forward tip thereof and the other of said jaw elements having an irrigation and suction catheter passing therethrough and exiting at a forward tip thereof.

7. A surgical device comprising a jaw pair in combination with means for actuating said jaw pair, said jaw pair comprising a first fixed jaw element and a second movable jaw element, said second movable jaw element being pivotally connected to said first fixed jaw element, one of said jaw elements having a laser fiber passing therethrough and exiting at a forward tip thereof and the other of said jaw elements having an irrigation and suction catheter passing partially therethrough and exiting generally medially along a length thereof.

8. A surgical device comprising a jaw pair in combination with means for actuating said jaw pair, said jaw pair comprising a first fixed jaw element and a second movable jaw element, said second movable jaw element being pivotally connected to said first fixed jaw element, one of said jaw elements having a laser fiber passing therethrough and exiting at a forward tip thereof and the other of said jaw elements having an irrigation and suction catheter passing partially therethrough, said other of said jaw elements further including at least two serrated teeth with avoid therebetween communicating with a cavity beneath said teeth and within said other of said jaw elements, wherein said catheter is operable to irrigate and suction through said cavity and between said teeth.

9. The jaw pair of claim 8 wherein said cavity exits said other of said jaw elements at a forward tip thereof.

10. A surgical device comprising a jaw pair in combination with means for actuating said jaw pair, said jaw pair comprising a first fixed jaw element and a second movable jaw element, said second movable jaw element being pivotally connected to said first fixed jaw element, one of said jaw elements having an irrigation and suction catheter passing partially therethrough, said one jaw element further including at least two serrated teeth with a void therebetween communicating with a cavity beneath said teeth and within said jaw element, wherein said catheter is operable to irrigate and suction through said cavity and between said teeth.

11. A laparoscopic forceps comprising:
a tubular housing having first and second ends;
a handle connected to said first end of said housing;
a pair of jaws connected to said second end of said housing;
jaw actuation means for actuating said pair of jaws via said handle;
laser means extending at least partially through
said housing and one jaw of said pair of jaws to a forward tip of said one jaw; and
irrigation means extending at least partially through said housing to said pair of jaws.

12. The laparoscopic forceps of claim 11 wherein said irrigation means extends to about a forward tip of one jaw of said pair of jaws.

13. A laparoscopic forceps comprising:
a tubular housing having first and second ends;
a handle connected to said first end of said housing;
a pair of jaws connected to said second end of said housing;
jaw actuation means for actuating said pair of jaws via said handle;
laser means extending at least partially through said housing and one jaw of said pair of jaws to a forward tip of said one jaw; and
suction means extending at least partially through said housing to said pair of jaws.

14. The laparoscopic forceps of claim 13 wherein said suction means extends to about a forward tip of one jaw of said pair of jaws.

15. A laparoscopic forceps comprising:
a tubular housing having first and second ends;
a handle connected to said first end of said housing;
a pair of jaws connected to said second ends of said housing;
jaw actuation means for actuating said pair of jaws via said handle;
laser means extending at least partially through said housing and one jaw of said pair of jaws to a forward tip of said one jaw; and cauterization means extending at least partially through said housing to said pair of jaws.

* * * * *